United States Patent [19]
Frey et al.

[11] Patent Number: 5,536,470
[45] Date of Patent: Jul. 16, 1996

[54] TEST CARRIER FOR DETERMINING AN ANALYTE IN WHOLE BLOOD

[75] Inventors: Günter Frey, Ellerstadt; Doris Horn, Ketsch, both of Germany

[73] Assignee: Boehringer Mannheim GmbH, Mannheim, Germany

[21] Appl. No.: 78,268

[22] PCT Filed: Feb. 26, 1992

[86] PCT No.: PCT/DE92/00154

§ 371 Date: Jul. 6, 1993

§ 102(e) Date: Jul. 6, 1993

[87] PCT Pub. No.: WO92/15879

PCT Pub. Date: Sep. 17, 1992

[30] Foreign Application Priority Data

Feb. 28, 1991 [DE] Germany .................. 41 06 293.0

[51] Int. Cl.$^6$ .................................................. G01N 33/49
[52] U.S. Cl. .................. 422/56; 422/61; 436/166; 436/169
[58] Field of Search ................. 422/56, 58, 61, 422/101; 436/63, 66–67, 164, 166, 169–170

[56] References Cited

U.S. PATENT DOCUMENTS

| | | | |
|---|---|---|---|
| 3,630,957 | 12/1971 | Rey et al. | 252/408 |
| 3,663,374 | 5/1972 | Moyer et al. | 196/103.5 |
| 4,069,017 | 1/1978 | Wu et al. | 23/230 |
| 4,256,693 | 3/1981 | Kondo et al. | 422/56 |
| 4,315,890 | 2/1982 | Tamers | 422/61 |
| 4,376,634 | 3/1983 | Prior et al. | 436/502 |
| 4,791,060 | 12/1988 | Chandler | 422/61 |
| 4,824,639 | 4/1989 | Hildenbrand et al. | 422/56 |
| 4,865,813 | 9/1989 | Leon | 422/61 |
| 4,935,346 | 7/1990 | Phillips et al. | 422/58 |
| 5,169,787 | 12/1992 | Knappe et al. | 436/169 |

FOREIGN PATENT DOCUMENTS

| | | |
|---|---|---|
| 0217246 | 9/1985 | European Pat. Off. . |
| 0256806 | 8/1986 | European Pat. Off. . |
| 0274911 | 12/1987 | European Pat. Off. . |
| 0130335 | 1/1988 | European Pat. Off. . |

OTHER PUBLICATIONS

Wrasidlo et al, *Journal of Parenteral Science and Technolgy*, "The Structure and Some Properties of Graded Highly Asymmetrical Porous Membranes", vol. 38, No. 1, Jan.–Feb. 1984.

*Primary Examiner*—Lyle A. Alexander
*Attorney, Agent, or Firm*—Nikaido, Marmelstein, Murray & Oram

[57] ABSTRACT

Test carrier for the determination of an analyte from whole blood. Within a test field, it contains a reagent system. The test field has a sample application side to which the blood sample is fed, and a detection side on which, as a result of the analysis reaction, an optically detectable change occurs. It is designed so that the red blood corpuscles cannot gain access from the sample application side to the detection side, and it contains pigment particles for optical blockage of the red blood pigment.

Reliable separation in combination with simple manufacture is achieved in that the test field (5) has a combined blood pigment separation and detection layer (1) which, in a single, very thin homogeneous layer, fulfils the functions of separation of the red blood corpuscles and optical detection. It is formed from a dispersion or an emulsion of a polymeric film former which, in homogeneous distribution, contains the pigment, the polymeric film former, the color formation reagent of the reagent system and a swelling agent.

12 Claims, 3 Drawing Sheets

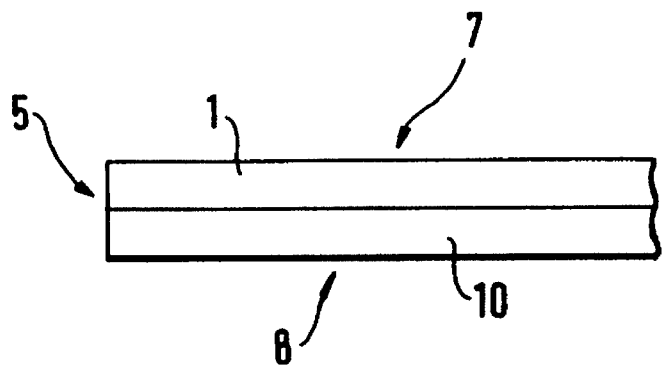
Fig. 4
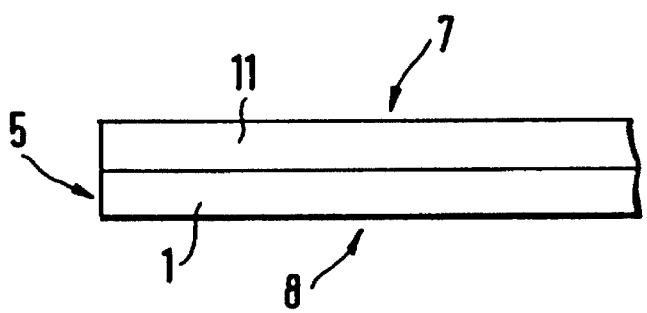
Fig. 5
Fig. 6
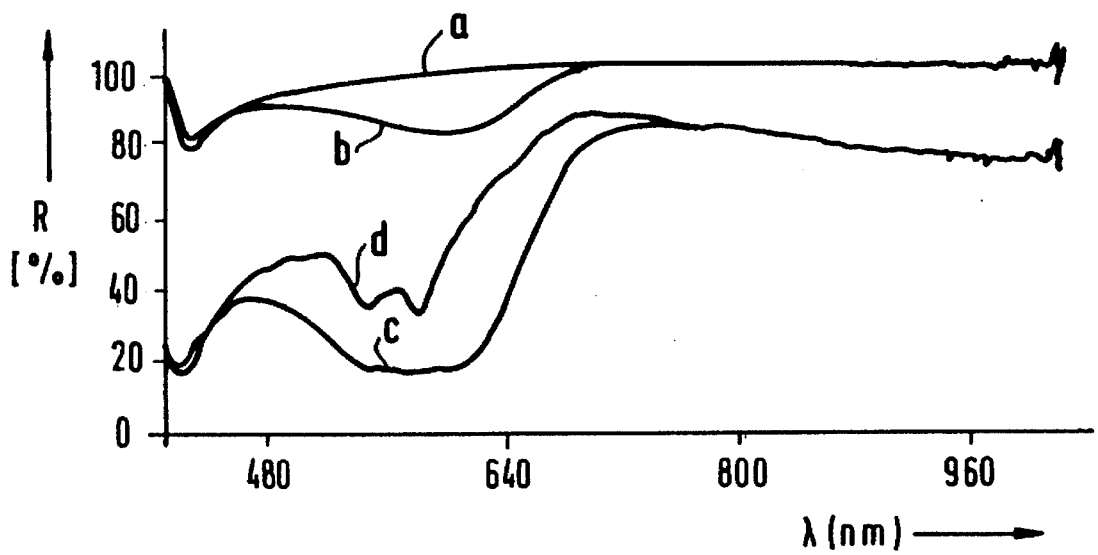

TEST CARRIER FOR DETERMINING AN ANALYTE IN WHOLE BLOOD

BACKGROUND OF THE INVENTION

1. Field of the Invention

The invention relates to a test field for a test carrier for the determination of an analyte from whole blood with the aid of a reagent system contained in the test carrier, said reagent system comprising a colour formation reagent, with a test field which has a sample application side, to which the blood sample is fed, and a detection side on which, as a result of reaction of the analyte with the reagent system, an optically detectable change occurs, the test field being designed so that erythrocytes contained in the sample do not gain access to the detection side.

2. Description of the Related Art

For the qualitative or quantitative analytical determination of constituents of blood, so-called carrier-bound tests are increasingly being used. In these, a reagent system is embedded in at least one test field of a solid test carrier, said test field consisting of a single layer or a plurality of layers, said test carrier being brought into contact with the sample. The reaction of sample and reagent system gives rise to an optically detectable change, in particular to a colour change which can be evaluated visually or with the aid of an instrument, usually by reflection photometry. Instead of leading to a colour change, the reaction may also give rise to the occurrence of, or to a change in, some other optically detectable signal, for example, fluorescence or luminescence.

Test carriers (which in the English-language literature are frequently also called "solid reagent analysis elements") are often designed as test strips, which essentially consist of a longitudinal carrier layer made of a plastic material, and a single test field or a plurality of test fields applied to it. However, test carriers are also known in which, analogously to a photographic slide, a test field is surrounded by a plastic frame.

Carrier-bound tests are characterised in particular in that they are easy to use. It is all the more unfortunate that, in the majority of test carriers known to date, the blood cannot be used directly as whole blood. Rather, it is necessary to separate the red blood corpuscles (erythrocytes) in order to obtain colourless plasma or serum. This is usually done by centrifuging. However, this involves an additional operation requiring a relatively large amount of blood and expensive equipment.

Many attempts have therefore been made to provide test carriers which permit analytical determinations to be made directly from blood. One can distinguish two fundamentally different possible solutions.

In the first attempted solution, evaluation of the colour change visually or with the use of equipment takes place on the same side of the test field as that to which the sample is applied. In this arrangement, the test field is constructed so that the analyte from the sample penetrates to the reagents through the test field surface, whereas the erythrocytes are retained. After a defined time, the blood sample is wiped or washed from the test field surface and the colour change is observed. Examples of such test carriers are described in U.S. Pat. No. 3,630,957 and in EP-B-130 335 and EP-A-0 217 246.

In the second attempted solution, the sample is applied to one side of the test field (sample application side), and the colour change on the other side (detection side) is recorded.

A major advantage of this method of detection is that the blood need not be wiped or washed off. For this reason, these test carriers are also called non-wipe ("NW")-test carriers.

With the wiping operation there is eliminated not only a tedious operation, but also a possible source of error which may result from imprecise observance of the point in time at which the blood must be removed. However, this attempted solution is especially difficult to embody. An erythrocyte or blood pigment filter is required which on the one hand reliably retains the intensely colouring constituents of blood but on the other hand allows the analyte to pass through completely and sufficiently rapidly. It is proving extraordinarily difficult to find a test field composition which meets these requirements.

In U.S. Pat. No. 3,663,374 and U.S. Pat. No. 4,256,693, a membrane filter is used. Although membrane filters are in principle suitable for filtering off erythrocytes, their use in test carriers has not proved successful. The same applies to the combination of the membrane filter with a glass-fibre layer also disclosed in these U.S. patents, said glass-fibre layer being intended to prevent blockage of the membrane filter with coarser particles. The manufacture of test carriers of this type would be very expensive, without satisfactory functioning being achieved.

U.S. Pat. No. 4,069,017 and a plurality of patents from the same applicant also address the possibility of providing, in a test carrier, an intermediate layer preventing the passage of erythrocytes, said intermediate layer at the same time containing radiation-blocking constituents to ensure that the light rays of the evaluation instrument cannot penetrate the erythrocyte-containing layer. However, this specification contains no details as to how the intermediate layer could be structured in the individual case in order to achieve the filtering of erythrocytes.

U.S. Pat. No. 4,824,639 describes the use of an asymmetrical membrane, such as that known for industrial separation procedures (reverse osmosis), for the purposes of erythrocyte separation. The membrane is manufactured in a coagulation procedure, by immersing a partially or completely gelatinised layer into a coagulation bath, and may also contain reagents. In this arrangement, the optical evaluation is said to be possible both from the blood application side (after wiping) and from the opposite side.

In EP-A-0 302 287 a test field is disclosed which has a composite layer which is manufactured by applying, in a liquid form, a detection layer containing the colour formation reagent on to a base layer which faces the sample application side. The base layer contains a polymeric film former, diatomaceous earth and a pigment. The detection layer contains a polymeric film former which, during application in a liquid form, partially penetrates the base layer and forms a transition zone in which the erythrocytes are retained.

The problem caused by the pigment constituents of the blood is further exacerbated by the fact that the capillary blood usually used, which is obtained by puncturing the skin, is inevitably partially haemolysed owing to the associated mechanical stresses, i.e., it contains blood pigment liberated from erythrocytes which have been destroyed. Although the haemolysed proportion is generally smaller than 0.1%, owing to its intense colour the liberated blood pigment still causes measuring inaccuracies even when the erythrocytes have been separated completely.

Since none of the previously known embodiments of an NW test carrier with erythrocyte separation exhibits satisfactory properties in every respect, in a commercially available embodiment of such a test carrier, separation of erythrocytes has been completely dispensed with, and distortion due to the intense red colour has been compensated for in the measuring technique with the aid of measurement at two different wavelengths. However, this impairs the measuring accuracy because the dark colour of the blood substantially reduces (by about a half) the signal difference, that is, the difference in the measured diffuse reflection within the measuring range of the test. Furthermore, the cost of instrumental evaluation is greatly increased, and visual checking of the colour change is impossible.

SUMMARY OF THE INVENTION

The aim of the invention is to make available for an NW test carrier a test field which permits reliable separation of the blood pigment, and rapid and intense formation of the optical detection signal (and, consequently, a high degree of measuring accuracy). At the same time it should be as easy to manufacture as possible.

In a test field of the type described in the preamble, the aim is achieved in that said test field has a combined blood pigment separation and detection layer which is formed from a dispersion or emulsion of a polymeric film former, said dispersion or emulsion containing, in homogeneous distribution, a pigment in a concentration of at least 30% by weight relative to the solid substance content of the film-forming mass, the polymeric film former, the colour formation reagent and a swelling agent, the swelling properties of the swelling agent being so good that the optically detectable change on the detection side is measurable after a maximum of one minute.

Dispersion film formers contain microscopic polymer particles which are insoluble in the carrier fluid (usually water), said particles being dispersed in the carrier fluid in an extremely fine distribution. When during formation of the film, the fluid is removed by evaporation, the particles move closer together until finally they touch. Due to the large forces occurring in this arrangement, and an increase in surface energy associated with formation of the film, the particles coalesce to form an essentially sealed film layer. Further details may be found, for example, in the article entitled "Latex film formation" by J. W. Vanderhoff in Polymer News 1977, pages 194 to 203.

Alternatively, an emulsion of the film former can also be used, in which the film former is dissolved in a solvent. The dissolved polymer is emulsified in a carrier fluid which is immiscible with the solvent.

Polyvinyl esters, polyvinyl acetates, polyacryl esters, polymethylacrylic acid, polyvinyl amides, polyamides and polystyrene are especially suitable as polymers for such film formers. In addition to homopolymers, mixed polymerisates e.g. of butadiene, styrene or maleic acid esters are also suitable.

The mean particle diameter of the pigment particles is preferably between 0.2 and 1 μm. Titanium dioxide is a widely available pigment which is also especially suitable for the invention.

The properties of the blood pigment separation and detection layer naturally depend not only on the film former, pigment and swelling agent, but also on the constituents of the test formulation which are contained in this layer. In addition to the actual reagent system, this usually also comprises auxiliary materials such as, for example, detergents, buffers and protective colloids.

As a result of this multiplicity of possible variants, it is not possible to state universal principles governing the quantitative composition of the layer-forming mass from which the blood pigment separation and detection layer is formed. On the basis of the information given here, however, the skilled person can, of course, test a selected composition, and optimise the formulation of the layer-forming mass for a specific application.

At a value of at least 30% by weight, and preferably at least 40% by weight relative to the total solids content of the layer-forming mass, the proportion of pigment is unusually high. Even with extreme layer thinness of the blood pigment separation and detection layer, this results in good radiation-blocking properties, i.e. the red colour on the sample application side does not interfere with the optical evaluation.

Surprisingly it was found that, by adding a swelling agent (i.e. a substance which increases its volume by absorbing water) with good swelling properties, not only is a layer obtained which is relatively quickly penetrated by the sample fluid but, despite this opening effect of the swelling agent, good blood pigment separation properties result. On the basis of the explanations given here, the required quality and quantity of the swelling agent can be established empirically for a specific layer composition. In any case, the swelling properties should be at least so good that, for a test in which the speed of the colour formation—as for example in the conventional glucose detection reaction—is predominantly dependent on penetration of the sample fluid through the layer, the optically detectable reaction is measurable after a maximum of one minute.

Methyl vinyl ether maleic acid anhydride copolymer has proved an especially suitable swelling agent.

From the experiments performed in connection with the present invention it can be inferred that film former and pigment should be in a roughly equal ratio to one another by weight. Depending on the circumstances in the individual case, weight ratios of the film former to the pigment of between 1:10 and 2:1 prove preferable.

As a rule it is advantageous if the total proportion of the sum of film former and pigment in the solid substance content of the film-forming mass is relatively high (usually over 70%). However, in connection with formulations which, on account of peculiarities of the analysis reaction, require an unusually high proportion of the reagent system by weight, positive results have also been achieved with a solid substance content of film former and pigment of 40% relative to the solid substance content of the film-forming mass. Inert inorganic particles with a mean particle diameter of considerably more than 1 μm, which are devoid of or have poor pigment properties, such as for example diatomaceous earth (kieselguhr, should be contained in the film-forming mass either not at all, or only in a very low concentration of less than 10%.

The manufacture of the combined blood pigment separation and detection layer from a homogeneous dispersion of the named constituents gives rise to a practically homogeneous layer structure. In this, the blood pigment separation and detection layer according to the invention is fundamentally different from the asymmetrical membrane according to U.S. Pat. No. 4,824,639 mentioned in the preamble.

An important point is that the combined blood pigment separation and detection layer is exceptionally thin. The mean dry layer thickness is preferably smaller than 0.05 mm, especially preferably smaller than 0.025 mm, and most especially preferably smaller than 0.015 mm.

Apart from ease of use, the test carrier according to the invention is characterised by an extremely short reaction time and intense colour formation. Furthermore, the test field is self-metering. From a sample applied in excess (for example between 5 µl and 50 µl) it absorbs only a reproducible fraction (for example 2 µl).

The invention represents a fundamental departure from the NW test fields proposed to date. Whereas, in the earlier attempts, the test field usually comprised a composite layer containing separate layers or zones, of which one was used for separation of erythrocytes and another for detection via a colour formation reaction, according to the invention the two functions are combined in a single, homogeneously composed layer, namely the blood pigment separation and detection layer. The test field preferably consists only of the blood pigment separation and detection layer. Since this is extremely thin and absorbs only a small amount of fluid, it is possible to work with an extremely small blood sample. In exceptional cases, however, the blood pigment separation and detection layer may be combined with other test layers, for example a layer previously positioned on the sample application side, said layer inducing lateral spreading (spreading layer), or a reagent layer containing reagents which are incompatible with the reagents contained in the blood pigment separation and detection layer.

The blood pigment separation and detection layer may be applied with its detection side on a transparent carrier film. According to an especially advantageous alternative, however, it is impregnated into an open-pore composite fibre structure.

According to another especially preferred embodiment, the blood pigment separation and detection layer may be applied to a microporous plastic layer (membrane) by direct coating of the membrane. In this arrangement, combination of the blood pigment separation and detection layer with an asymmetrical membrane has proved especially favourable, said membrane for its part having erythrocyte-separating properties. Membranes of this type are now being sold for a variety of filtration purposes. An overview can, for example, be found in the article entitled "The structure and some properties of graded highly asymmetrical porous membranes", by W. Wrasidlo and K. J. Mysels, Journal of Parenteral Science and Technology, 1984, pages 24 to 31. Of particular advantage here is the fact that the blood pigment separation and detection layer not only separates blood corpuscles, but also brings about effective separation of the blood pigment insofar as this is present in concentrations which occur in practice. Experimentally it has been established that the layer according to the invention is even suitable for processing samples with up to 0.5% haemolysis. This value exceeds with a good safety margin the haemolysis values of at most about 0.1% which occur in practice. If the blood corpuscles are separated completely from blood with 0.5% haemolysis, the resulting serum still has a strong red colour. However, if such a serum is applied from the sample application side to a blood pigment separation and detection layer according to the invention, the blood pigment is separated so completely that the analytical measurement on the evaluation side is practically unimpaired by it within the measuring accuracy.

BRIEF DESCRIPTION OF THE DRAWINGS

The invention is explained in detail below by means of an exemplifying embodiment represented diagrammatically in the following figures:

FIG. 4 and FIG. 5: Greatly enlarged diagrammatic views of a cross-section through alternative embodiments of test fields;

FIG. 6: A plurality of spectra relating to one of the examples;

DETAILED DESCRIPTION OF THE PREFERRED EMBODIMENT

Figure 1:
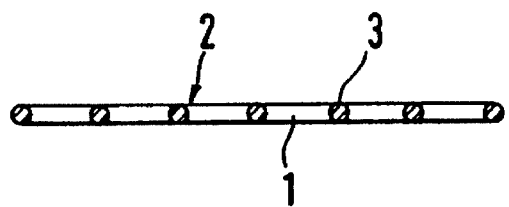
FIG. 1: A greatly enlarge diagrammatic view of a cross-section through a test field structure which is suitable for the invention, said test field structure being in the wet state.
Figure 2:
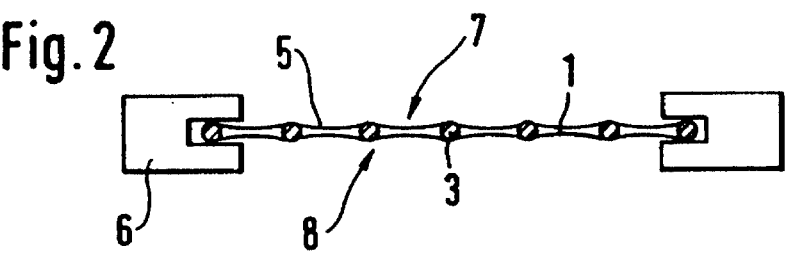
FIG. 2: A greatly enlarged diagrammatic view of a cross-section through a test carrier according to the invention.

FIGS. 1 and 2 show, in cross-section, a test field material in which the erythrocyte separation and detection layer 1 is impregnated into a fibre composite structure 2. Here the term "fibre composite structure" signifies any composite of threads or fibres having the properties required for the invention, namely a very small thickness (at most 0.1 mm, preferably 0.02 to 0.06 mm) and adequate open-porosity. The fibre composite structure can preferably be a tissue or a knitted fabric. A very thin and loose mat can also be used, though this is less preferable.

The composite fibre structure may consist of monofilamentous threads or of multifilamentous fibres (i.e. fibres which comprise many individual threads and are twisted), the monofilamentous threads having proved especially successful.

Figure 3:
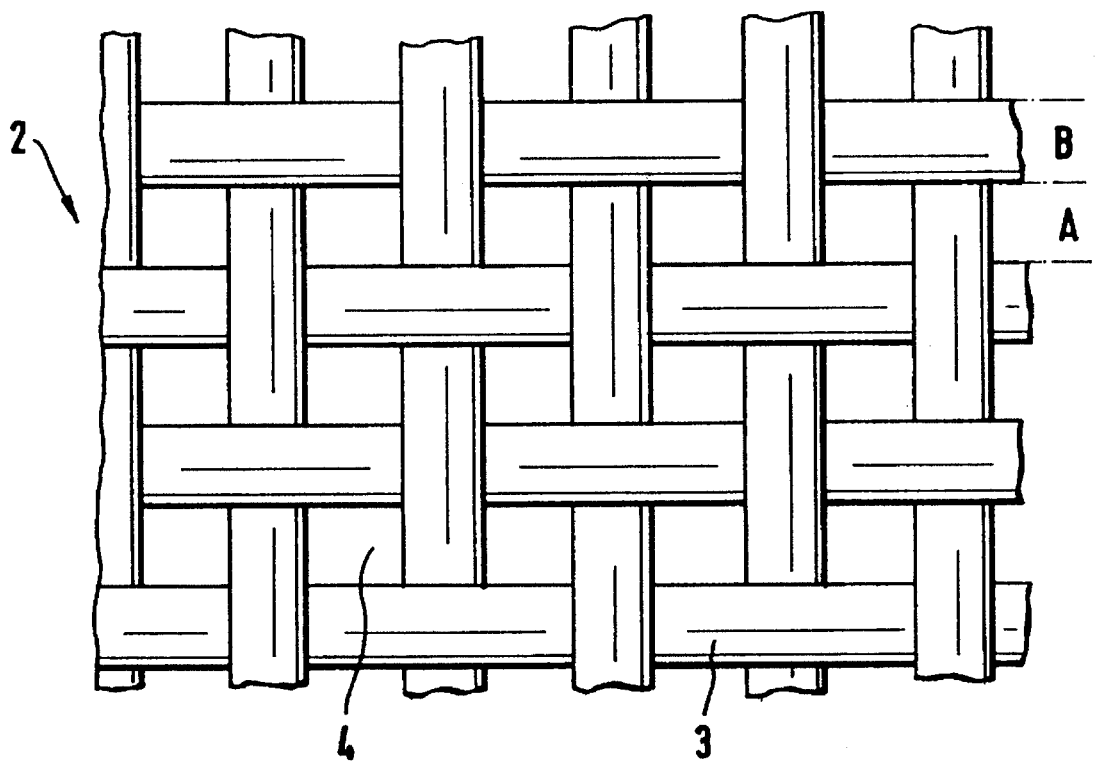
FIG. 3: A top view of a composite fibre structure suitable for the invention, from an electron microscopy image.

FIG. 3 shows the typical structure of a monofilamentous tissue suitable for the invention. The threads 3 have a loose, lattice-like structure with open pores 4. The pore size A should be between 0.02 and 0.06 mm, preferably between 0.03 and 0.04 mm. In the case of square pores shown, the term "pore size" signifies their edge length. With the use of a pore shape diverging from the square shape, the pore size is defined as the square root of the mean pore cross-section.

The thickness B of the threads from which the composite fibre structure is formed is preferably between 0.02 and 0.06 mm, especially preferably between 0.03 and 0.04 mm. Polyethylene has proved successful as thread material. However, other materials are also suitable.

As mentioned, the test field of a test carrier according to the invention preferably consists only of the blood pigment separation and detection layer applied to a carrier material. Such a test carrier is shown diagrammatically in FIG. 2. The test field, indicated overall by the number 5, is held by a frame 6. The sample is applied from the sample application side 7. The optical evaluation takes place on the detection side 8.

The disclosed structure of a blood pigment separation and detection layer which is impregnated into an open-pore composite fibre structure is characterised above all in that it is self-supporting, i.e. no transparent carrier film is necessary as an underlay. However, in this arrangement it is important that the pores of the composite fibre structure are so completely closed that the blood applied to the sample application side 7 cannot gain access through small crevices or cracks because, owing to the intense red colour of blood, even relatively small amounts can distort the result of the optical measurement.

In order to ensure this it is advantageous if, during the manufacture of the test field material, the substances of which the blood pigment separation and detection layer consists are processed to form a film-forming impregnating mass which is impregnated into a ribbon of carrier material consisting of the open-pore composite fibre structure in such a way that the impregnating mass extensively penetrates into the pores of the carrier material. The impregnating mass is then smoothed with the aid of a smoothing tool. Thereafter, the ribbon of test field material is dried without contact.

Overall, the impregnating mass is applied so that the hollow spaces of the carrier material are practically completely filled and the threads are thinly covered with impregnating mass on both sides. The state after smoothing is shown in highly diagrammatic form in FIG. 1.

Due to the drying process, the layer thickness of the impregnating mass is reduced. This gives rise to a characteristic structure, in which the surface of the test layer between the threads is slightly concavely curved, as indicated in FIG. 2.

A blood pigment separation and detection layer impregnated into a composite fibre structure, as explained by means of FIGS. 1 to 3, is preferred above all when a self-supporting test layer material is desired in which the layer is in contact with the surrounding air on both sides. This applies above all to reagent systems which include oxidation steps with the aid of the oxygen in air.

FIG. 4 shows a composition of the test field such as is suitable for a test system which functions independently of the oxygen in air. In this arrangement, the blood pigment separation and detection layer 1 is coated on to a transparent plastic film 10.

FIG. 5 shows the embodiment in which the blood pigment separation and detection layer is coated on to a microporous plastic layer (membrane) 11. The membrane preferably faces the blood application side 7, as shown.

The following examples serve to explain the invention in more detail.

EXAMPLE 1

To manufacture a blood pigment separation and detection layer for the quantitative analysis of glucose from whole blood, a dispersion of the following composition is manufactured:

Formulation:

|  | Original weight (g) | |
| --- | --- | --- |
|  | absolute | solid substance content |
| Polyvinyl propionate (PVP)-/polyvinyl acetate (PVA) dispersion (50% in water) | 5 g | (2.5) |
| Titanium dioxide powder in water (1:1 paste) | 10 g | (5.0) |
| Methyl vinyl ether maleic acid anhydride copolymer (Gantrez AN 139; 5% in water) | 8 g | (0.4) |
| Potassium dihydrogen phosphate | 0.27 g | (0.3) |
| Disodium hydrogen phosphate dihydrate | 0.28 g | (0.3) |
| Glucose oxidase | 30 KU | (0.3) |
| Peroxidase | 500 KU | (0.15) |
| Methylaminobenzthiazolinone hydrazone (MBTH) | 0.2 g | (0.2) |
| 3-(dimethylamino)benzoic acid | 0.2 g | (0.2) |
| Distilled water | 4.0 g |  |
| Sodium hydroxide | 0.1 g | (0.1) |

This mixture is applied to a monofilamentous polyethylene or nylon tissue approximately 0.05 mm thick with the aid of a doctor (doctor gap approximately 0.08 mm), and then dried directly with hot air for approximately 30 min at 60° C. without contact.

Depending on the glucose concentration, with blood containing glucose the reagent layer thus manufactured shows well graduated blue reaction colours which can be measured with a remission photometer at 565 nm. If the measuring instrument is calibrated with the blank value of the reaction layer to 100% remission and with a black film to 4% remission, the following remissions are obtained for the corresponding glucose concentrations in the blood:

| Glucose in blood mg/dl | |
| --- | --- |
| 0 | 100% |
| 40 | 81% |
| 80 | 67% |
| 100 | 62% |
| 300 | 39% |
| 400 | 34% |
| 500 | 30% |
| 600 | 26% |

In FIG. 6, four different spectra of remission photometric measurements are shown, in which the remission (in %) is plotted against the wavelength (in nanometres). Spectra a, b and c relate to test fields according to example 1, with a glucose-free sample (a), a glucose content of 30 mg/dl (b) and a glucose content of 700 mg/dl (c). The typical absorption minimum of the indicator MBTH is observed. The difference between spectrum a and spectra b and c represents the useful signal at the selected measurement wavelength.

Spectrum d relates to a case in which the sample contains 30 mg/dl glucose as in example b, but a detection layer is used in which the blood pigment separation is incomplete. The red blood pigment gives rise to a pronounced minimum in the range important for the measurement. It is clear that this results in an intolerable distortion of the measuring signal results from this.

EXAMPLE 2

In order to test the influence of various concentrations of pigment and film former on the blood pigment separation property, the formulation of example 1 was varied in respect of the content of these two components.

Figure 7:
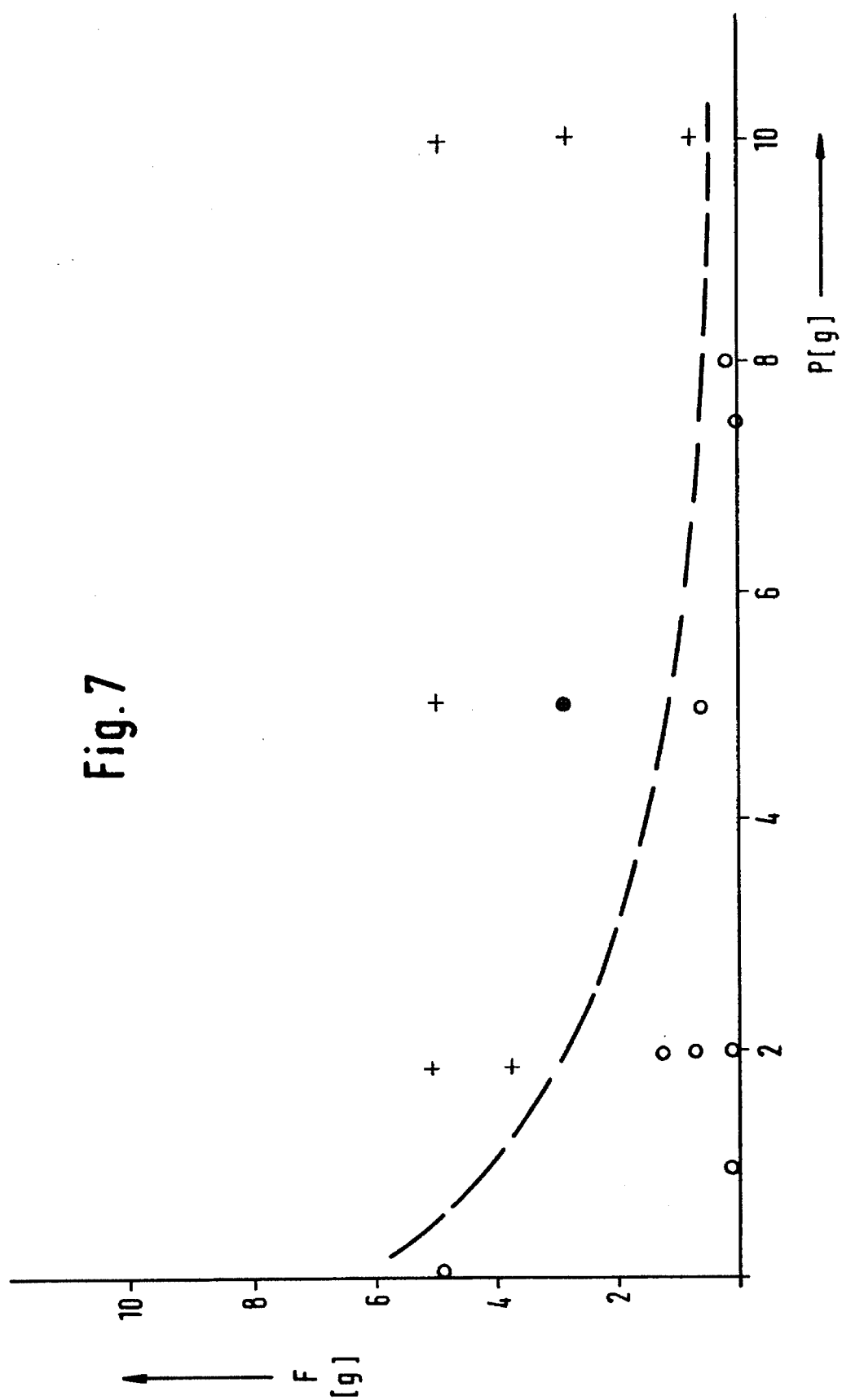
FIG. 7: A graphical view to explain the influence of the composition of the film-forming mass in one of the examples.

The results are shown in FIG. 7, the solid substance weight of the pigment P being plotted on the abscissa, and the solid substance weight of the film former F on the ordinate. The hollow circles signify compositions with which the blood pigment separation property achieved was unsatisfactory, while the + symbols signify compositions whose function was satisfactory. The asterisks signify compositions with which, although adequate separation of erythrocytes is achieved, the radiation-blocking properties of the layer are inadequate. The value pair from example 1 is indicated by an encircled + symbol. It is characterised by an especially good blood pigment-separating effect.

The results show that the separating effect achieved is not good if both the amount of pigment and the amount of film former used are very small. A satisfactory result can be achieved both by increasing the proportion of pigment and by increasing the proportion of film former. Especially good results are achieved if the two are in a roughly balanced ratio to one another and their total weight in the layer-forming formulation is sufficiently high.

EXAMPLE 2a

In order to document the influence of various swelling agents, the Gantrez AN 139 in the formulation of example 1 was replaced with Keltrol F (manufacturer: Kelco/Ail International GmbH, Hamburg, Germany). The table below shows, for the two formulations, the course of the measured diffuse reflection (% rem) for two different blood samples. We see that, with the use of the swelling agent Gantrez AN 139, a stable value already arises after 30 seconds, remaining unchanged for the next 30 seconds. When Keltrol F is used, the end value is approached more slowly. Here too, however, with appropriate calibration a reliable measurement is possible after less than one minute with good accuracy.

|  | Time since application of the sample (sec) | Blood 1 (%) rem. | Blood 2 |
| --- | --- | --- | --- |
| Keltrol F | 10 | 52.8 | 36.7 |
|  | 20 | 47.2 | 23.1 |
|  | 30 | 45.9 | 18.7 |
|  | 40 | 44.8 | 17.2 |
|  | 50 | 44.2 | 16.5 |
|  | 60 | 44.0 | 16.3 |
| Gantrez AN 139 | 10 | 45.4 | 22.2 |
|  | 20 | 44.6 | 17.6 |
|  | 30 | 44.1 | 16.9 |
|  | 40 | 44.0 | 16.2 |
|  | 50 | 44.0 | 16.2 |
|  | 60 | 44.0 | 16.2 |

Comparably good results are not achieved with swelling agents with inferior swelling properties, for example alginate, which is frequently used in test layer formulations.

EXAMPLE 3

Manufacture of a test field for a test carrier for the detection of triglycerides in blood.
Formulation:

|  | Original weight (g) | |
| --- | --- | --- |
|  | absolute | solid substance content |
| Polyvinyl propionate dispersion (50% in water) | 7 g | (3.5) |
| Titanium dioxide | 4 g | (4.0) |
| Keltrol F (0.5% in H$_2$O) | 27 g | (0.15) |
| Adenosine-5'-triphosphate disodium salt | 60 mg | (0.06) |
| Magnesium sulphate-7-hydrate | 60 mg | (0.06) |
| Dioctyl sodium sulfosuccinate | 100 mg | (0.1) |
| 1-(4-methylphenyl)-semicarbazide | 1.5 mg | (0.002) |
| Detergent Triton X-100 | 200 mg | (0.2) |
| Cholesterol esterase | 3 KU | (0.25) |
| Glycerophosphate oxidase | 0.8 KU | (0.01) |
| Glycerokinase | 3 KU | (0.15) |
| Peroxidase | 500 MU | (0.15) |
| 4(5)-(4-dimethylaminophenyl)-2-(4-hydroxy-3,5-dimethoxyphenyl)-5(4)-methylimidazole × HCl | 50 mg | (0.05) |
| Phosphate buffer 0.2 M/pH 7.5 | 4 g | (0.05) |

From the formulation components a homogeneous coating mass is manufactured. The pH is checked and adjusted to pH 7.5 if necessary. Immediately thereafter, the mass is scraped into a multifilamentous polyethylene tissue (thickness approximately 0.04 mm) in a wet film thickness of approx. 0.06 mm, and dried in a circulating air drying cabinet for approx. 60 minutes at 50° C.

During the analysis of blood samples containing triglyceride, well graduated blue colours are obtained within a concentration range of 50 to 300 mg/dl, said colours being evaluable by remission photometry at 660 nm.

EXAMPLE 4

In order to test the usability of various pigment substances, the formulation of example 1 was changed in respect of the pigment, and experiments were made with various concentration ratios. In the table below are stated the dry substance weights of formulations which were tested and which show satisfactory blood pigment separation properties:

| Polyvinyl propionate | Barium sulphate |
| --- | --- |
| 5 g | 10 g |
| 5 g | 1 g |
| Polyvinyl propionate | Orgasol 2002 |
| 5 g | 10 g |
| 5 g | 1 g |

The barium sulphate had a mean particle size of 0.6 μm (manufacturer: Merck, Darmstadt, Germany).

Orgasol 2002 is a polyamide particle powder with pigment properties, which is manufactured by Atochem, Elf-Aquitaine, Ortez, France. The mean particle size is 0.4 μm.

EXAMPLE 5

Manufacture of a reagent film for the reductive detection of glucose.
Formulation:

|  | Original weight (g) | |
| --- | --- | --- |
|  | absolute | solid substance content |
| Keltrol F (Manufacturer: Kelco/Ail International GmbH, Hamburg, Germany) 2% dissolved in citrate buffer 0.5 M/pH 7 | 20 g | (0.4) |
| Titanium dioxide in citrate buffer 0.5 M/pH (1:1 paste) | 40 g | (20.0) |
| Polyvinyl propionate (PVP)-/polyvinyl acetate (PVA) (50% dispersion in water) | 5 g | (2.5) |
| Sodium nonyl sulphate solution (15% in water) | 3 g | (0.4) |
| Tartrazine (manufacturer: Merck) | 2 g | (2.0) |
| Tetraethylammonium chloride | 7 g | (7.0) |
| 2,18-phosphoromolybdic acid | 16 g | (16.0) |
| Kollidon 25 (manufacturer: BASF, Ludwigshafen, Germany) | 2 g | (2.0) |
| N,N-bis-hydroxyethyl-p-nitroso-aniline | 140 mg | (0.140) |
| GOD | 2 g | (2.0) |
| Water | 40 g | — |

The formulation is homogenised and scraped on to a Pokalon film (manufacturer: Lonza, Switzerland) in a thickness of 0.1 mm. It is then dried at 60° C. The reagent film obtained shows excellent erythrocyte-separating properties and, depending on the glucose concentration, an intense colour formation.

This example shows that a blood pigment separation and detection layer according to the invention can also be manufactured in cases in which, on account of the specific peculiarities of the test, the soluble constituents of the reagent system must be present in a relatively high concentration. In the present case, the total dry weight of the indicator combination of tetraethylammonium chloride and 2,18-phosphoromolybdic acid is roughly within the same order of magnitude as the total dry weight of pigment and film former.

We claim:

1. Test carrier for the determination of an analyte in whole blood using a reagent system having a colour formation reagent, said test carrier comprising:

a test field portion for receiving and reacting with a blood sample, said test field portion comprising a sample application side for receiving said blood sample, and a detection side opposite the sample application side for detecting an optically detectable change as a result of a reaction of the analyte with the reagent system, the test field portion also comprising a film layer having a homogenous layer structure and which performs separation of erythrocytes and of the analyte blood pigment and performs a color formation for detection without needing to compensate for blood color, due to a portion of said blood sample appearing on said detection side being substantially free from blood pigment, said film layer being made from a film forming mass by evaporating a carrier liquid from a dispersion or emulsion of a polymeric film former, said dispersion or emulsion comprising, in homogeneous distribution, a pigment in a concentration of at least 30% by weight relative to the film-layer, the polymeric film former, the colour formation reagent, and a swelling agent, said pigment preventing the blood pigment from affecting the optically detectable change on the detection side of the test field portion, wherein swelling properties of the swelling agent are selected such that the optically detectable change on the detection side is measurable after a maximum of one minute.

2. Test carrier according to claim 1, wherein a mean thickness of the film layer is no greater than 0.05 mm.

3. Test carrier according to claim 1, wherein the film layer is impregnated into an open-pore composite fibre structure wherein pores of the composite fibre structure are closed thereby.

4. Test carrier according to claim 3, wherein a mean pore size of the composite fibre structure is between 0.02 and 0.06 mm.

5. Test carrier according to claim 1, wherein the film layer is coated on to a microporous plastic layer.

6. Test carrier according to claim 5, wherein the microporous plastic film is disposed adjacent the sample application side of the test carrier.

7. Test carrier according to claim 5, wherein the microporous plastic film comprises an asymmetrical structure, and at least partially separates erythrocytes.

8. Test carrier according to claim 1, wherein the film layer is coated on to a plastic film.

9. Test carrier according to claim 1, wherein the swelling agent comprises a methyl vinyl ether maleic acid copolymer.

10. A test carrier according to claim 2, wherein said mean thickness is no greater than 0.025 mm.

11. A test carrier according to claim 2, wherein said mean thickness is no greater than 0.015 mm.

12. A test carrier according to claim 4, wherein the mean pore size of the composite fiber structure is between 0.03 and 0.05 mm.

* * * * *